US009625309B2

(12) United States Patent
Baboulaz et al.

(10) Patent No.: US 9,625,309 B2
(45) Date of Patent: Apr. 18, 2017

(54) DEVICE FOR DETERMINING A BIDIRECTIONAL REFLECTANCE DISTRIBUTION FUNCTION OF A SUBJECT

(71) Applicant: Ecole Polytechnique Fédérale de Lausanne (EPFL), Lausanne (CH)

(72) Inventors: Loïc Arnaud Baboulaz, Lausanne (CH); Gaël Georges Soudan, Morges (CH); Martin Vetterli, Grandvaux (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 14/559,726

(22) Filed: Dec. 3, 2014

(65) Prior Publication Data
US 2016/0161330 A1 Jun. 9, 2016

(51) Int. Cl.
*G03B 17/00* (2006.01)
*G01J 1/02* (2006.01)
*G01N 21/55* (2014.01)

(52) U.S. Cl.
CPC ............ *G01J 1/0271* (2013.01); *G01N 21/55* (2013.01)

(58) Field of Classification Search
USPC .................. 396/428, 419; 336/445
See application file for complete search history.

(56) References Cited

U.S. PATENT DOCUMENTS

| | | | | |
|---|---|---|---|---|
| 6,654,013 B1 * | 11/2003 | Malzbender | .......... | G06T 15/506 345/426 |
| 7,679,756 B2 * | 3/2010 | Sperling | ................. | G01J 3/504 356/446 |
| 8,149,268 B1 * | 4/2012 | Meyers | .................. | H04N 5/144 348/42 |
| 2004/0036882 A1 * | 2/2004 | Perlin | .................... | G01N 21/55 356/446 |

(Continued)

OTHER PUBLICATIONS

Tom Malzbender et al.; Polynomial Texture Maps; Hewlett-Packard Laboratories; 2001; http://www.hpl.hp.com/ptm; 10 pages.

(Continued)

*Primary Examiner* — Clayton E Laballe
*Assistant Examiner* — Warren K Fenwick
(74) *Attorney, Agent, or Firm* — Taft Stettinius & Hollister LLP (57) ABSTRACT

A device for determining a bidirectional reflectance distribution function of a subject, including a light source for producing an incident light that is directed onto a subject at a predetermined zenith angle and at a predetermined azimuth angle, an element for displacing the light source at any location on the periphery of a hemispherical area centered on the subject, an element for measuring the bidirectional reflectance distribution function of the subject from one fixed location that is preferably aligned with a normal direction defined by the subject, a control unit adapted to control the element for displacing and/or the element for measuring. The element for displacing includes an arc- (Continued)

shaped arm at one end fixedly connected to the light source and slideably connected to a first support to adjust the zenith angle, and an element for pivoting the first support about the normal direction to permit adjustment of the azimuth angle.

22 Claims, 7 Drawing Sheets

(56) References Cited

U.S. PATENT DOCUMENTS

| | | | | |
|---|---|---|---|---|
| 2004/0061784 A1* | 4/2004 | Perlin | ............... | G01N 21/55 |
| | | | | 348/207.99 |
| 2005/0068537 A1* | 3/2005 | Han | ............... | G01N 21/4795 |
| | | | | 356/446 |
| 2007/0258093 A1* | 11/2007 | Sieck | ............... | G01N 21/55 |
| | | | | 356/446 |
| 2012/0035884 A1* | 2/2012 | Ingram | ............... | G01S 7/411 |
| | | | | 702/181 |
| 2013/0271461 A1* | 10/2013 | Baker | ............... | G06T 15/50 |
| | | | | 345/420 |
| 2014/0152985 A1* | 6/2014 | Buchhorn | ............... | G01J 1/0242 |
| | | | | 356/326 |
| 2014/0354801 A1* | 12/2014 | Baboulaz | ............... | G01N 21/55 |
| | | | | 348/135 |

OTHER PUBLICATIONS

F.E. Nicodemus et al.; Geometrical Considerations and Nomenclature for Reflectance; U.S. Department of Commerce, National Bureau of Standards; Oct. 1977; 67 pages.

* cited by examiner

DEVICE FOR DETERMINING A BIDIRECTIONAL REFLECTANCE DISTRIBUTION FUNCTION OF A SUBJECT

FIELD OF THE INVENTION

The present invention relates to a device for determining a bidirectional reflectance distribution function of a subject.

BACKGROUND OF THE INVENTION

Much recent work in realistic image synthesis has focused on the use of actual data measurements of a surface of three-dimensional object for rendering said surface with parametric texture maps in a computer graphics system.

One conventional method consists to characterize the reflectance properties of a surface by its bidirectional reflectance distribution function (BRDF), as explained in the document "Geometric Considerations and Nomenclature for Reflectance", U.S. Department of Commerce, National Bureau of Standards, published in October 1977 and written by Nicodemus, F. E., Richmond, J. C., and Hsia, J. J. One known technique for measuring the BRDF of a surface is image based and consists to photograph a surface under varying lighting conditions so as to determine a bidirectional reflectance distribution of the surface. In particular, the document "Polynomial Texture Maps", published in 2001 and written by Malzbender, T., Gelb, D., and Wolters, H., relates to an apparatus for in situ surface reflectance measurement, wherein 50 inward-pointing light sources are distributed on a small, portable hemispherical frame, each light source illuminating the surface from a different known direction and a camera positioned at the apex of the hemispherical frame capturing the light reflected by the surface.

However, this later solution raises several problems. Firstly, the accuracy of the parametric texture map is directly dependent on the number of light sources of the hemispherical frame. A great number of light sources are thus needed to get a sufficient accuracy. Furthermore, this accuracy is not always possible considering that one light source may deliver a light slightly different from another one. The measurements made by the camera must thus be corrected afterwards by the computer graphics system to correct this lack of homogeneity. Finally, in this solution, the positions of the light sources on the periphery of the hemispherical surface are predetermined and can not be modified. Therefore, the modification of the incident direction of the light sources can not be made or made only by providing other hemispherical surfaces comprising other locations for the light sources corresponding to other incident directions thereof.

A need therefore exists to develop a device for determining a bidirectional reflectance distribution function of a subject which overcomes the deficiencies of the above mentioned device.

SUMMARY OF THE INVENTION

In this view, the present invention relates to a device for determining a bidirectional reflectance distribution function of a subject comprising:
 a light source for producing a incident light and directing said incident light onto a subject at a predetermined zenith angle and at a predetermined azimuth angle;
 means for displacing said light source at any location on the periphery of a hemispherical area centered on the subject;
 means for measuring the bidirectional reflectance distribution function of the subject from one fixed location, said fixed location being preferably aligned with a normal direction defined by the subject;
 a control unit adapted to control said displacing means and/or said measuring means;
 wherein said displacing means comprises:
  an arc-shaped arm at one end of which is fixedly connected the light source, said arc-shaped arm being slideably connected to a first support through sliding means, thus permitting the adjustment of said zenith angle; and
  means for pivoting said first support about said normal direction, thus permitting the adjustment of said azimuth angle.

Important features of the device are defined in dependent claims 2 to 20.

Thus configured, the device of the present invention permits to determine the bidirectional reflectance distribution function of a subject by using only one light source. Therefore, compared to the apparatus of Malzbender et al., it provides a less expensive and less complex solution. Furthermore, it avoids that downward image corrections have to be made by the computer graphics system when several non-homogeneous light sources are used.

Finally, the device of the present invention permits to position the light source at any location on the periphery of a hemispherical area, thus potentially improving the accuracy of the parametric texture map.

BRIEF DESCRIPTION OF THE DRAWINGS

Other features and advantages of the present invention will appear more clearly from the detailed description of one embodiment of the invention which is presented solely by way of a non-restricted example and illustrated by the attached drawings in which.

DETAILED DESCRIPTION OF EMBODIMENTS OF THE INVENTION

Figure 1:
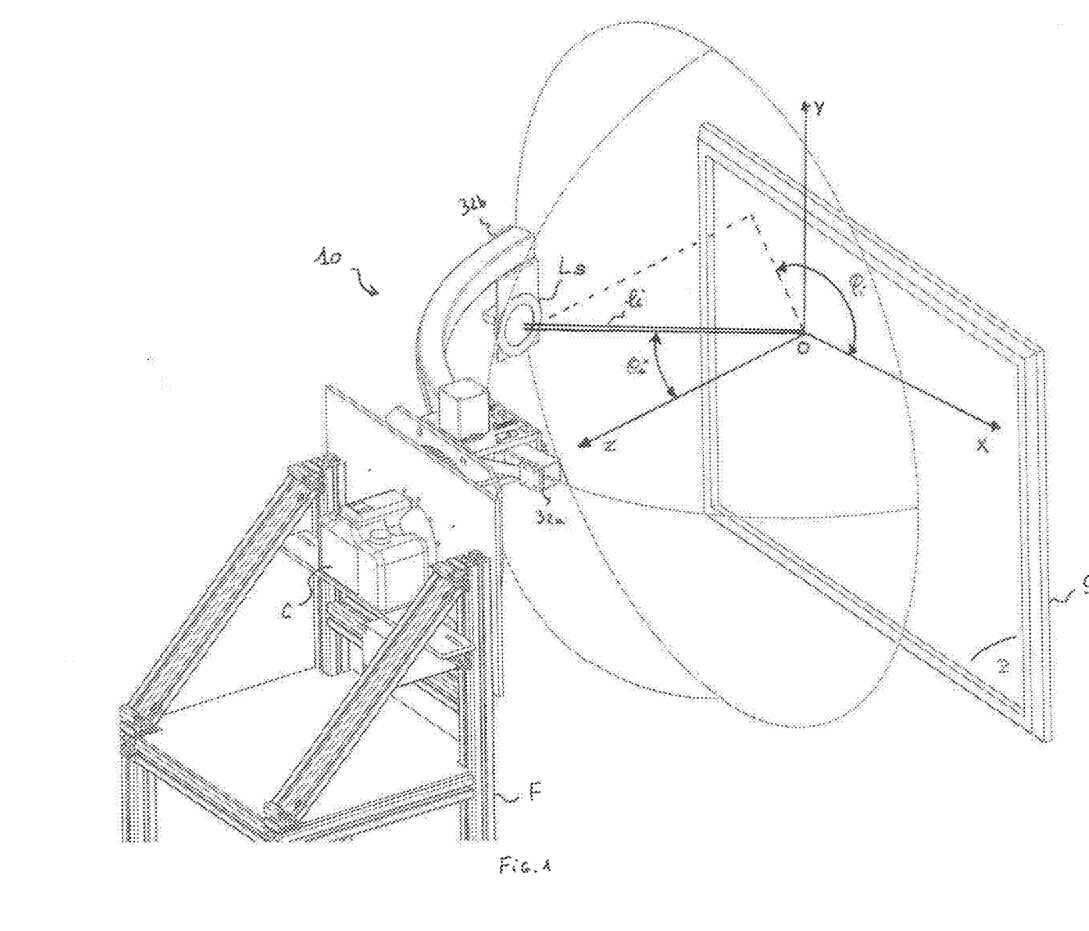
FIG. 1 is a rear perspective view of a device according to an embodiment of the present invention in a specific arrangement for determining the parametric texture map of a painting.

In reference to FIG. 1, there is shown an embodiment of the device according to the present invention, said device 10 being arranged in front of a subject S in such a manner to determine the parametric texture map of said subject. In the embodiment shown, this subject S is a painting defined by a plane P intended to receive the incident light li coming from the light source LS of the device 10. This light source LS is preferably a LED but the present invention is not limited to such a type. As described in the following paragraphs, the device 10 is thus configured so as to permit a displacement of the light source LS at any location on the periphery of a hemispherical area centered on a point O of said plane P. Therefore, the incidence of the incident light li may vary relative to said plane P. In particular, when the plane P is defined by a normal direction Z at point O and by a direction X orthogonal to said normal direction Z and a direction Y orthogonal to said direction X and said normal direction Z, the incidence of the incident light li may be defined by a zenith angle $\theta_i$ and by an azimuth angle $\phi_i$, the zenith angle $\theta_i$ corresponding to the angle between the direction defined by the incident light li and the normal direction Z and the azimuth angle $\phi_i$ corresponding to the angle between a projection line of the incident light li to the plane P and the direction X. In the embodiment shown, the orientation of the subject S is chosen so as to orientate the plane P vertically and the plane defined by the directions X and Z horizontally. In an alternative embodiment of the invention, the orientation of the subject S may also be chosen so as to orientate the plane P horizontally and the plane defined by the directions X and Z vertically. The light reflected by the subject S is sensed or captured by specific sensing means incorporated in the device 10. In the embodiment shown, said sensing means consist in a camera C pointed toward the subject S, said camera being substantially aligned with the normal direction Z. In further embodiments of the present invention, said sensing means may also consist in a video camera and/or may be orientated obliquely relative to said normal direction Z. The numeric data registered by the sensing means for several positions of the light source LS will be treated afterwards by a data processing unit, preferably a computer, in operative communication with the sensing means so as to permit the measurement of the BRDF of the subject S, the combination of said data processing unit and said sensing means defining at least partially the measuring means of independent claim 1. Further details relative to the method permitting to calculate the BDRF of the subject based on the numeric data registered by the sensing means are given in the document "Polynomial Texture Maps" mentioned above and incorporated by reference herein.

In the embodiment shown in FIG. 1, the device 10 is fixedly connected to a frame F distant from the subject S in the normal direction Z. The distance between said frame F and said subject S in the normal direction Z may advantageously be variable so as to position point O nearby the center of the hemispherical area defined by the device 10 while preventing any physical contact between said device 10 and said subject S. Accordingly, the frame F and/or the subject S may be mounted on rails or wheels.

Figure 2:
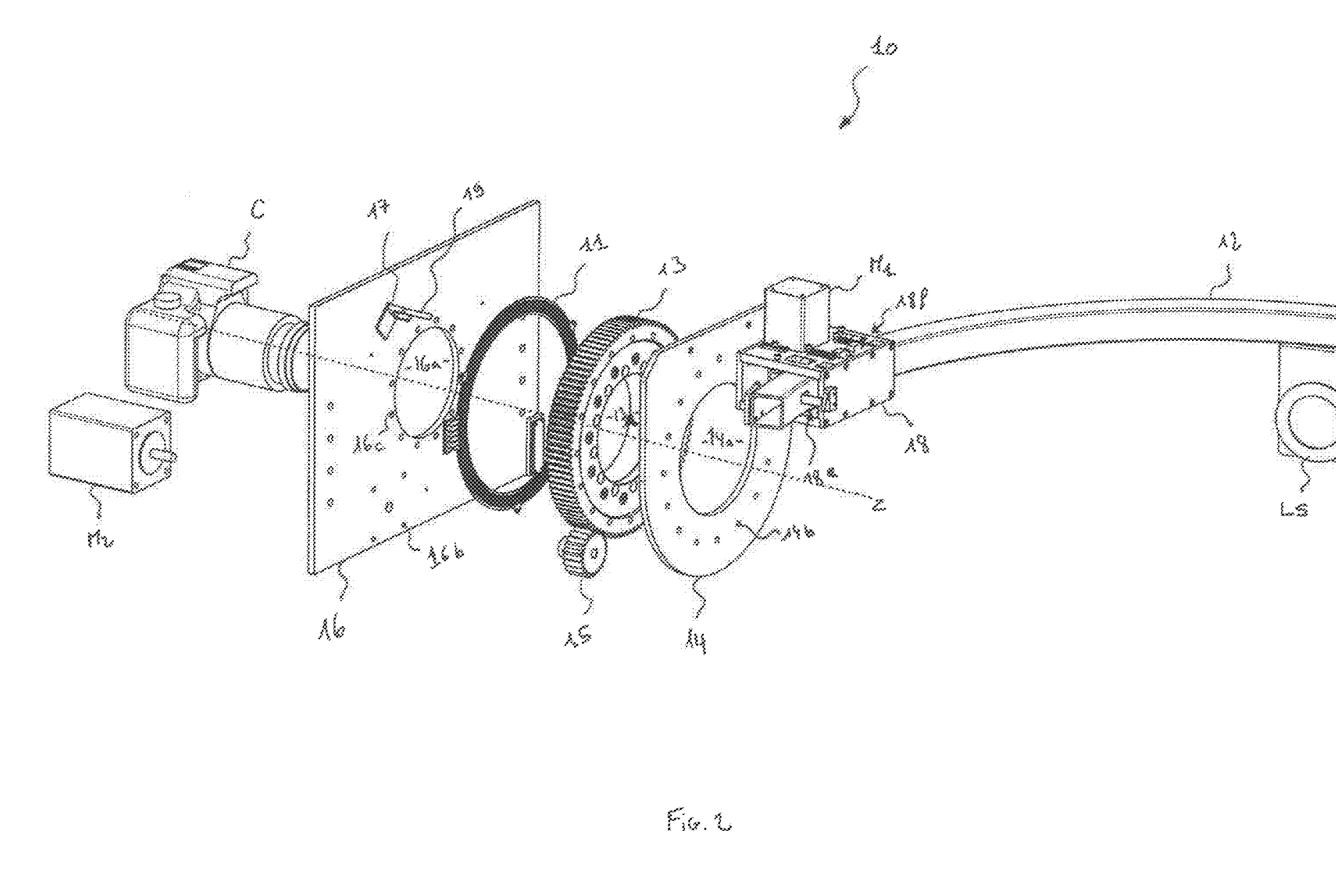
FIG. 2 is an exploded view of the device illustrated in FIG. 1.

In reference to FIG. 2, the different constituting parts of the device 10 are illustrated in their respective position before their assembling and their connection to the frame F. The main parts of said device 10 comprise an arc-shaped arm 12 at one end of which is fixedly connected the light source LS, said arc-shaped arm being a metallic profile with a square cross-section, said arm defining substantially a quadrant and being slideably connected to a first plane support 14, perpendicular to the normal direction Z, so as to permit the adjustment of the zenith angle $\theta_i$. In particular, the arc-shaped arm 12 is partially received in a parallelepiped casing 18 that is fixedly connected to the side of the first support facing the subject S, said casing having a top side defined by a top plate 18c, a bottom side opposite thereto defined by a bottom plate 18d, a front side defined by a front plate 18a, a rear side opposite thereto defined by a rear plate 18b, and two opposite lateral sides 18e, 18f, said lateral sides being unsealed so as to permit the movement of the arc-shaped arm inside the casing. The means permitting the displacement of the arc-shaped arm 12 inside the casing 18 will be described in the following paragraphs. The first support 14 is provided with a disc-shaped aperture 14a, that is adapted to partially receive a lens of the camera C, and with a plurality of threaded through holes 14b, regularly spaced-apart at the periphery thereof, said threaded holes being adapted to receive the screws permitting the connection of a first toothed wheel 13 to the side of the first support facing the frame. Said first toothed wheel 13 meshes with a second smaller toothed wheel 15, said second toothed wheel being operationally coupled to a stepper motor M2 that induces its rotation around an axis parallel to the normal direction Z and thus, indirectly, the rotation of the first toothed wheel 13 around the normal direction Z. Therefore, due to the fixed connection of the first toothed wheel to the first support, the stepper motor M2 can swivel the first support 14 round the normal direction Z, thus permitting the adjustment of the azimuth angle $\phi_i$ of the incident light emitted by the light source LS. The device 10 may advantageously comprise a control unit (not shown) adapted to control the current received by the stepper motor M2 so that the first support 14 rotates around the axis Z until the arc-shaped arm 12 reaches a target position corresponding to a predetermined azimuth angle $\phi_i$ of the incident light li. In particular, the control unit may be configured to receive a signal emitted by a fork sensor 17, fixedly connected to the second support 16, when an opaque thin plate 19, fixedly connected to the first support 14, interrupts a beam of light transmitted by an emitter of said fork sensor before said beam of light is received by a receiver of said fork sensor. This interruption occurs when the first support 14 is in a reference position corresponding to a specific azimuth angle $\phi_o$ of the incident light li. Thus, the control unit can calculate the current to apply to the stepper motor M2 in accordance with the difference between the predetermined azimuth angle $\phi_i$ of the incident light li in the target position of the arc-shaped arm 12 and said specific azimuth angle $\phi_o$. Thereafter, by applying this current to the stepper motor M2, the arc-shaped arm 12 can be positioned in the target position. Advantageously, the reference position of the first support 14 may correspond to the position illustrated in FIG. 1.

Figure 4:
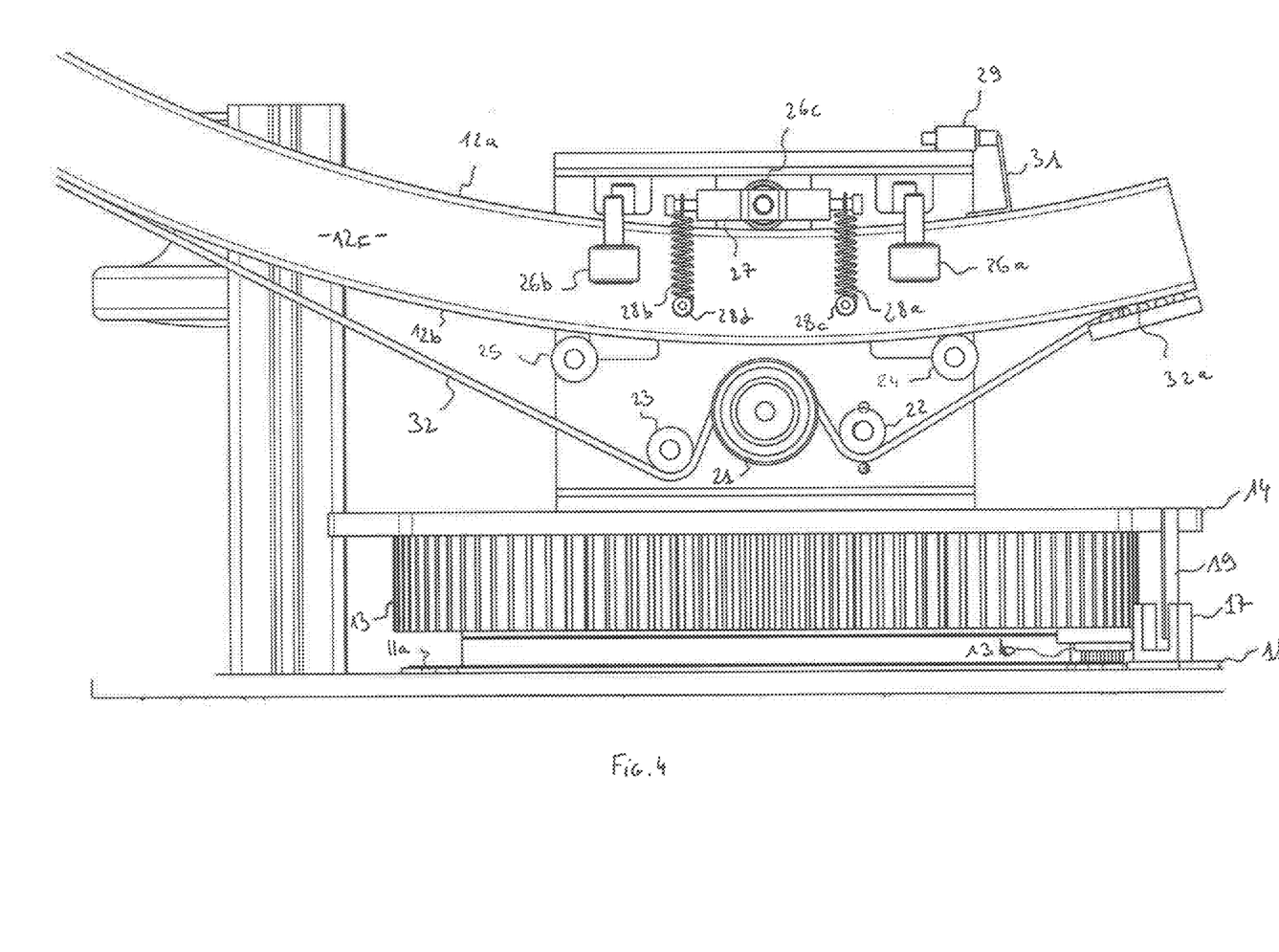
FIG. 4 is an enlarged top view of the device illustrated in FIG. 1, when the first motor and the top plate of the parallelepiped casing supporting said first motor are withdrawn.

As shown in FIG. 2, the first toothed wheel 13 is advantageously provided with a central disc-shaped aperture 13a that is axially aligned with the aperture 14a of the first support and that is adapted to partially receive the lens of the camera C. The stepper motor M2 is fixedly connected to a second plane support 16, axially distant from the first support 14 and parallel thereto, said second support being fixedly connected to the frame F. This second support 16 is also provided with a disc-shaped aperture 16a axially aligned with the aperture 14a of the first support and adapted to partially receive the lens of the camera C. The apertures 14a and 16a of the first and second supports, and the central aperture 13a of the first toothed wheel 13 may advantageously be centered on the normal direction Z for every position of the arc-shaped arm 12. The second support 16 is provided with a plurality of threaded through holes 16b so as to permit the threaded connection of the motor M2 thereto. Other through-holes 16c of the second support make easier the passing of electric cables through the device, said electric cables connecting in particular the light source LS to an external electric power source. Similar through holes may advantageously be formed inside the first support 14 and/or the first toothed wheel 13. Furthermore, the device 10 may advantageously comprise a ring-shaped current collector 11, as illustrated in FIGS. 2 and 4, including one or several circular conductive tracks 11*a*, said tracks being in electrical contact with a metallic brush 13*b*, fixedly connected to the side of the first toothed wheel 13 that faces the frame F. Thus, the electric cables connected to the brush 13*b* may be supplied with current through the ring-shaped current collector 11.

Figure 3:
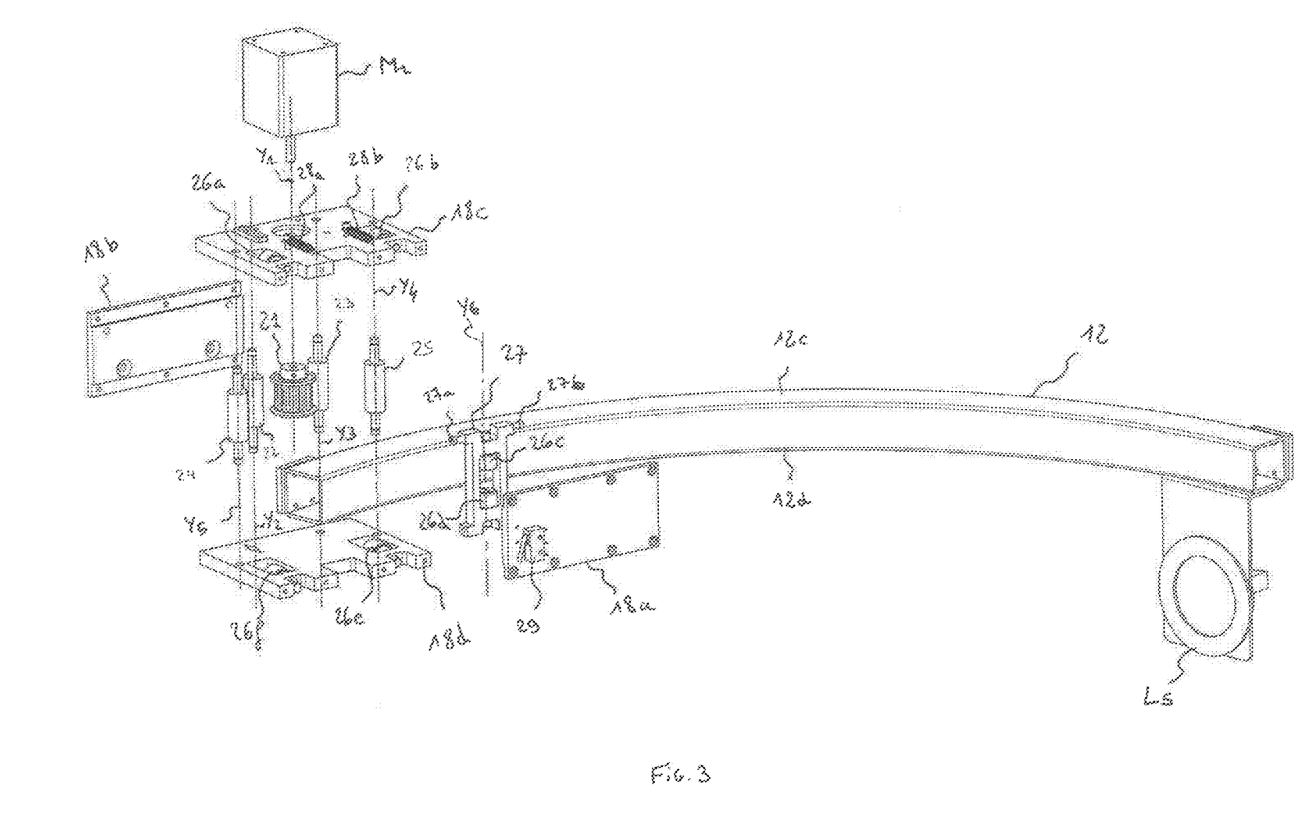
FIG. 3 is an enlarged exploded view of the specific means used for displacing the arc-shaped arm of the device illustrated in FIG. 2.

In reference to FIGS. 3 and 4, the means permitting the displacement of the arc-shaped arm 12 inside the casing 18 are illustrated.

These displacing means comprise means for sliding the arm and means for guiding the arm.

The sliding means comprise a semi-rigid belt 32 fixedly connected at its two free ends, respectively its proximal end 32*a* and its distal end 32*b* (see FIG. 1), to the arc-shaped arm 12, said belt extending along a rear side 12*b* of the arm and being partially and successively wound around a proximal tensioning roller 22, a drive roller 21 and a distal tensioning roller 23. The drive roller 21 pivots about a motor axis Y1, which is preferably parallel to the axis Y, under the action of a stepper motor M1 fixedly connected to the top plate 18*c* of the casing 18. This roller 21 is adapted to impart motion to the belt 32 by friction such that the distance between its proximal end 32*a*, and also its distal end 32*b*, and the motor axis Y1 is modified. The periphery of the drive roller 21 may advantageously be provided with a plurality of grooves so as to increase the friction between the belt 32 and the drive roller 21. The role of the proximal and distal tensioning rollers 22, 23, that freely pivot about pivot axes Y2 and Y3 parallel to the motor axis Y1, is to maintain the belt 32 under tension. The position of the tensioning roller 22 and/or of the tensioning roller 23 may advantageously be adjustable so as to permit the adjustment of the tension of the belt.

Figure 6:
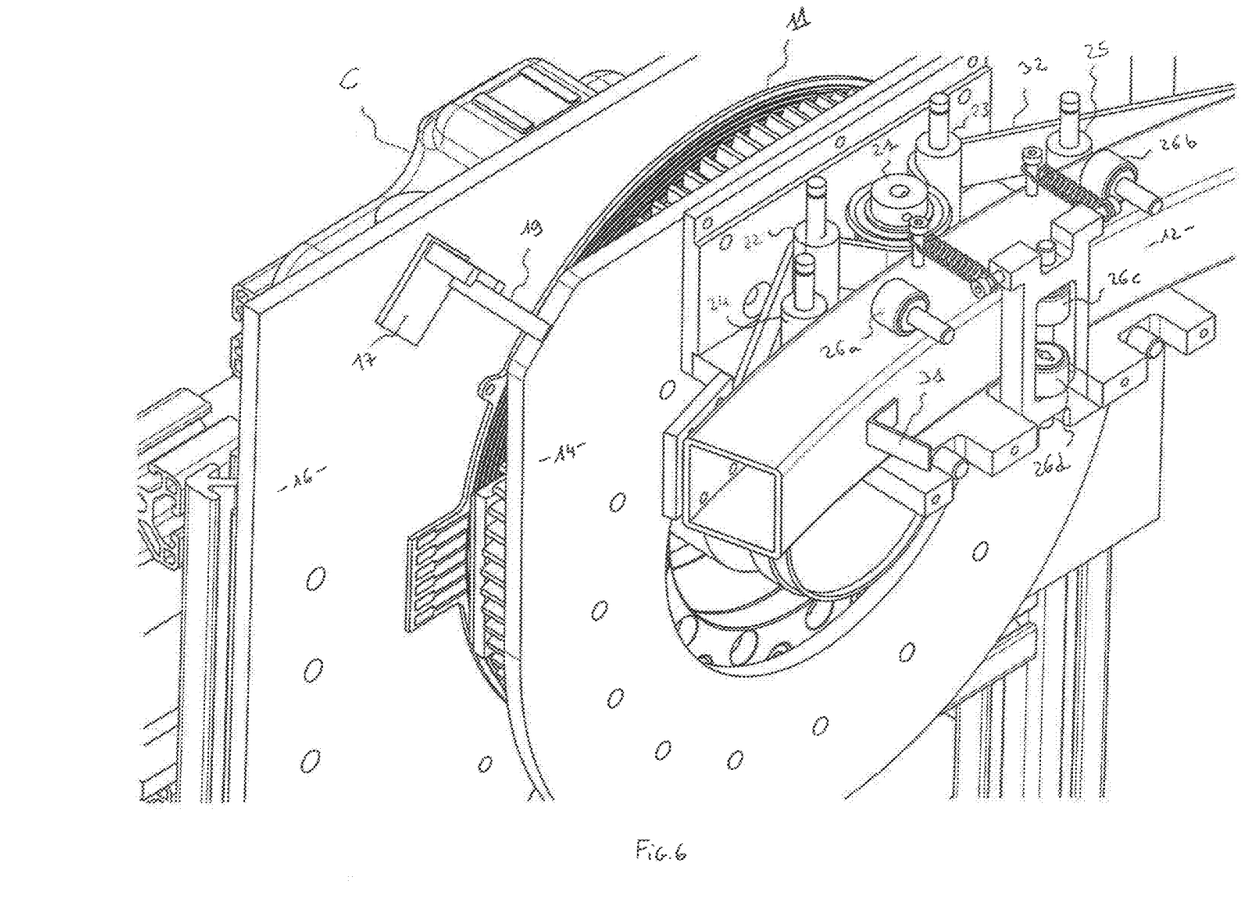
FIG. 6 is a view similar to FIG. 5, except that the first motor, the top plate and the front plate of the parallelepiped casing supporting said motor are withdrawn.

The guiding means are configured to force the arc-shaped arm 12 to make a circular path centered substantially on point O of the plane P. In the embodiment shown, the guiding means comprise two internal guiding rollers 26*c*, 26*d* in contact with a front side 12*a* of the arc-shape arm 12, said internal guiding rollers pivoting about a pivot axis Y6, which is parallel to the motor axis Y1, and two external guiding rollers 24, 25, respectively a proximal external guiding roller 24 and a distal external guiding roller 25, in contact with the rear side 12*b* of the arc-shaped arm 12, said external guiding rollers 24 and 25 pivoting respectively about pivot axes Y4 and Y5, which are parallel to the motor axis Y1. Advantageously, the two external guiding rollers 24, 25 are positioned such that the plane defined by the pivot axes Y4, Y5 are perpendicular to the plane defined by the motor axis Y1 and the pivot axis Y6 of the two internal guiding rollers 26*c*, 26*d*. As illustrated in FIGS. 4 and 6, the internal guiding rollers 26*c*, 26*d* are advantageously supported by a single bracket 27, said bracket being resiliently connected to the casing 18 at a proximal upper end 27*a* through a proximal compression spring 28*a* and at a distal upper end 27*b* through a distal compression spring 28*b*. In particular, the proximal compression spring 28*a*, respectively the distal compression spring 28*b*, extends between said proximal upper end 27*a*, respectively said distal upper end 27*b*, and a proximal connecting element 28*c*, respectively a distal connecting element 28*c*, which is fixedly connected to the top plate 18*c* of the casing 18.

As shown in FIGS. 3 and 6, the guiding means includes also two top guiding rollers 26*a*, 26*b* in contact with a top side 12*c* of the arc-shaped arm 12 and two bottom guiding rollers 28*e*, 28*f* in contact with a bottom side 12*d* of the arc-shaped arm 12. The top guiding rollers 26*a*, 26*b*, respectively the bottom guiding rollers 28*e*, 28*f*, are advantageously pivotally received in two corresponding recesses of the top plate 18*c*, respectively of the bottom plate 18*d*, of the casing 18. The top and bottom guiding rollers 26*a*, 26*b*, 26*e* and 26*f* are configured to keep substantially constant the distance between the arc-shaped arm 12 and a plane reference surface when the azimuth angle $\phi_i$ of the incident light is kept unchanged. In particular, when the arc-shaped arm 12 is substantially horizontal, as illustrated in FIG. 1, the guiding means permits to maintain said arm horizontal during its displacement, if the first support 14 does not pivot around the axis Z.

Figure 5:
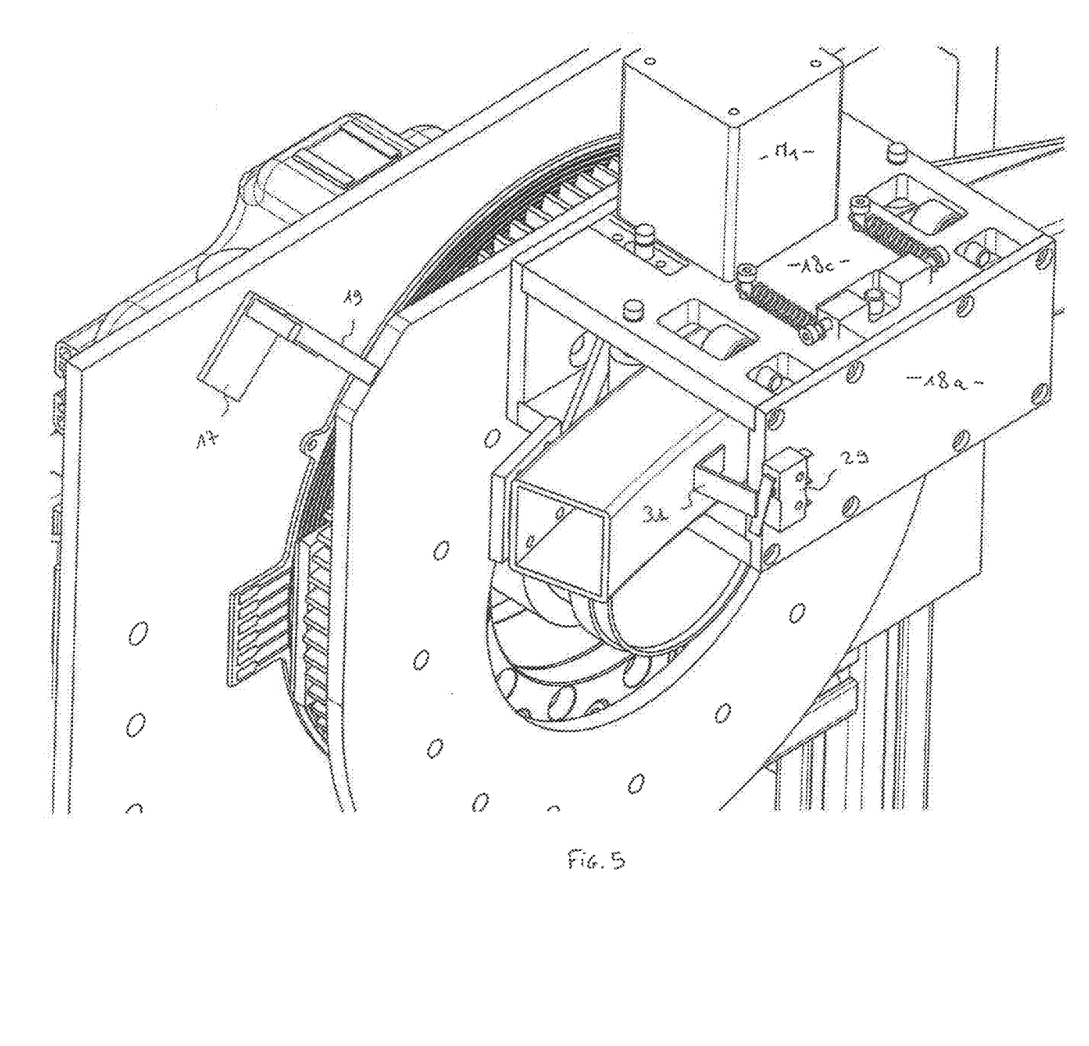
FIG. 5 is an enlarged front perspective view of the device illustrated in FIG. 1, in a first work position.

The sliding movement of the arc-shaped arm 12 is controlled by the control unit. In particular, the control unit is adapted to adjust the current received by the stepper motor M1 so that the drive roller 21 rotates around the axis Y1 until the arc-shaped arm 12 reaches a target position corresponding to a predetermined zenith angle $\theta_i$ of the incident light li. In particular, the control unit may be configured to receive a signal emitted by a contact sensor 29, fixedly connected to the casing 18, when a metallic T-shaped leg 31 fixedly connected to the arc-shaped arm 12, electrically contact said contact sensor 29, as illustrated in FIG. 5. This electric contact occurs when the arc-shaped arm 12 is in a reference position corresponding to a specific zenith angle $\theta_0$ of the incident light li. Thus, the control unit can calculate the current to apply to the stepper motor M1 in accordance with the difference between the predetermined zenith angle $\theta_i$ of the incident light li in the target position of the arc-shaped arm 12 and said specific zenith angle N. Thereafter, by applying this current to the stepper motor M1, the arc-shaped arm 12 can be positioned in the target position. Advantageously, the reference position of the arc-shaped arm may correspond to the position illustrated in FIG. 1, in which the specific zenith angle $\theta_0$ is between 85° and 90°.

Figure 7:
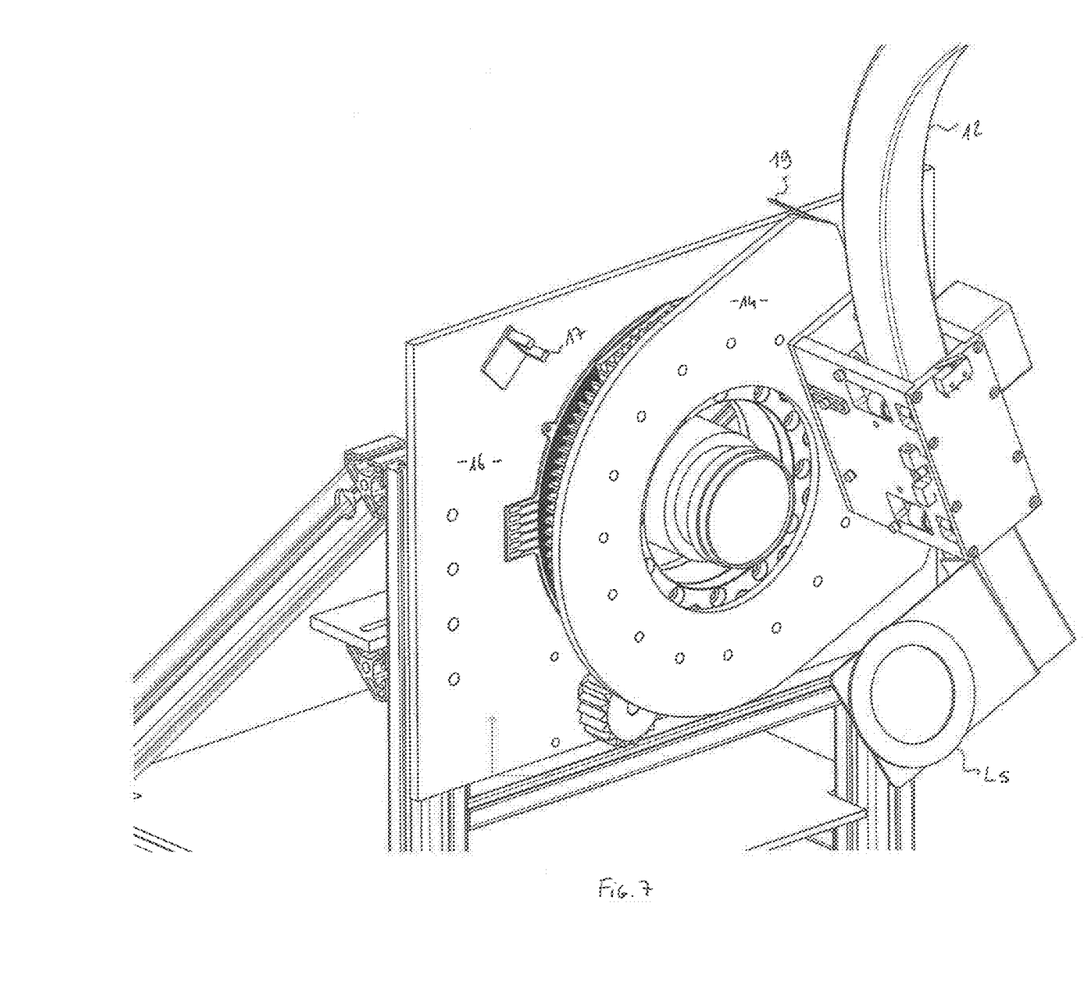
FIG. 7 is an enlarged front perspective view of the device illustrated in FIG. 1, in a second work position.

FIG. 7 illustrates the position of the arc-shaped arm 12 after successively a rotation of approximately 90° of the arc-shaped arm 12 around axis Y and a rotation of approximately 60° of the first support 14 around axis Z. In this specific position, the incident light li is substantially aligned with axis Z.

The above detailed description with reference to the drawings illustrates rather than limits the invention. There are numerous alternatives, which fall within the scope of the appended claims.

The invention claimed is:

1. Device for determining a bidirectional reflectance distribution function of a subject comprising:
    a light source for producing an incident light and directing said incident light onto a subject at a predetermined zenith angle and at a predetermined azimuth angle;
    means for displacing said light source at any location on the periphery of a hemispherical area centered on the subject;
    means for measuring the bidirectional reflectance distribution function of the subject from one fixed location, said fixed location being preferably aligned with a normal direction defined by the subject;
    a control unit adapted to control said displacing means and/or said measuring means;
    wherein said displacing means comprises:
        an arc-shaped arm at one end of which is fixedly connected the light source, said arc-shaped arm being slideably connected to a first support through sliding means, thus permitting the adjustment of said zenith angle; and means for pivoting said first support about said normal direction, thus permitting the adjustment of said azimuth angle.

2. The device according to claim 1, wherein the measuring means includes sensing means for sensing the light reflected from the subject.

3. The device according to claim 2, wherein the sensing means are positioned at the apex of the hemispherical area, which is aligned with the normal direction.

4. The device according to claim 3, wherein the sensing means includes a camera which receives the light reflected from the subject.

5. The device according to claim 2, wherein the sensing means includes a camera which receives the light reflected from the subject.

6. The device according to claim 1, wherein the light source is a LED.

7. Device for determining a bidirectional reflectance distribution function of a subject comprising:
a light source for producing an incident light and directing said incident light onto a subject at a predetermined zenith angle and at a predetermined azimuth angle;
means for displacing said light source at any location on the periphery of a hemispherical area centered on the subject;
means for measuring the bidirectional reflectance distribution function of the subject from one fixed location, said fixed location being preferably aligned with a normal direction defined by the subject;
a control unit adapted to control said displacing means and/or said measuring means;
wherein said displacing means comprises:
an arc-shaped arm at one end of which is fixedly connected the light source, said arc-shaped arm being slideably connected to a first support through sliding means, thus permitting the adjustment of said zenith angle; and
means for pivoting said first support about said normal direction, thus permitting the adjustment of said azimuth angle,
wherein the sliding means comprise a belt fixedly connected at its two free ends, respectively a proximal end and a distal end, to the arc-shaped arm, said belt being partially and successively wound around a proximal tensioning roller, a drive roller and a distal tensioning roller, said drive roller pivoting about a motor axis and being adapted to impart motion to said belt by friction such that the distance between said proximal end and said motor axis is modified, said proximal and distal tensioning rollers pivoting about pivot axes parallel to said motor axis and being adapted to maintain said belt under tension; and
wherein guiding means are provided so as to force the arc-shaped arm to make a circular path centered on the subject.

8. The device according to claim 7, wherein the drive roller is provided with a plurality of grooves at its periphery so as to increase the friction between the belt and the drive roller.

9. The device according to claim 8, wherein the arc-shaped arm is defined by an internal lateral side, oriented towards the subject, and an external lateral side, oriented in the opposite direction thereof, and wherein the guiding means comprise at least one internal guiding roller in contact with said internal lateral side and at least two external guiding rollers, respectively a proximal external guiding roller and a distal external guiding roller, in contact with said external lateral side, said external and internal guiding rollers pivoting about pivot axes parallel to the motor axis.

10. The device according to claim 7, wherein the arc-shaped arm is defined by an internal lateral side, oriented towards the subject, and an external lateral side, oriented in the opposite direction thereof, and wherein the guiding means comprise at least one internal guiding roller in contact with said internal lateral side and at least two external guiding rollers, respectively a proximal external guiding roller and a distal external guiding roller, in contact with said external lateral side, said external and internal guiding rollers pivoting about pivot axes parallel to the motor axis.

11. The device according to claim 10, wherein the plane defined by the motor axis and the pivot axis of the internal guiding roller is perpendicular to the plane defined by the pivot axes of the two external guiding rollers.

12. The device according to claim 10, wherein the arc-shaped arm is defined by a top side and a bottom side and wherein the guiding means comprise at least one top guiding roller in contact with said top side and at least one bottom guiding roller in contact with said bottom side, said top and bottom guiding rollers being adapted to keep substantially constant the distance between the arc-shaped arm and a plane reference surface when the azimuth angle of the incident light is kept unchanged.

13. The device according to claim 12, wherein the drive roller, the tensioning rollers, the external and internal guiding rollers and the top and bottom guiding rollers are encapsulated in a parallelepiped casing, said casing being positioned along the circular path of the arc-shaped arm and having two unsealed opposite lateral sides so as to permit the movement of said arc-shaped arm inside said casing.

14. The device according to claim 7, wherein a first stepper motor is operationally coupled to the drive roller to cause rotation thereof, said first stepper motor being controlled by the control unit.

15. The device according to claim 14, wherein the arc-shaped arm comprises a metallic leg protruding from one of its lateral sides, said leg being adapted to electrically contact a sensor when said arc-shaped arc is in a reference position corresponding to a specific zenith angle of the incident light, and wherein said sensor emits a signal to the control unit when said electric contact occurs, the control unit controlling thereafter the first stepper motor in accordance with the difference between the predetermined zenith angle of the incident light in a target position of the arc-shaped arm and said specific zenith angle of the incident light so as to position said arc-shaped arm in said target position.

16. The device according to claim 15, wherein the specific zenith angle is between 85° and 90°.

17. Device for determining a bidirectional reflectance distribution function of a subject comprising:
a light source for producing an incident light and directing said incident light onto a subject at a predetermined zenith angle and at a predetermined azimuth angle;
means for displacing said light source at any location on the periphery of a hemispherical area centered on the subject;
means for measuring the bidirectional reflectance distribution function of the subject from one fixed location, said fixed location being preferably aligned with a normal direction defined by the subject;
a control unit adapted to control said displacing means and/or said measuring means;

wherein said displacing means comprises:
- an arc-shaped arm at one end of which is fixedly connected the light source, said arc-shaped arm being slideably connected to a first support through sliding means, thus permitting the adjustment of said zenith angle; and
- means for pivoting said first support about said normal direction, thus permitting the adjustment of said azimuth angle;
- wherein the pivoting means comprises a first toothed wheel fixedly connected to the first support, said first toothed wheel meshing with a second toothed wheel, and wherein a second stepper motor is operationally coupled to said second toothed wheel to cause rotation thereof, said second stepper motor being controlled by the control unit.

18. The device according to claim 17, wherein the first support and/or the first toothed wheel are provided with a plurality of through-holes, said through-holes being adapted to partially receive at least one electric cable connecting the light source to a brush fixedly connected to the first toothed wheel, said brush being in electrical contact with at least one circular conductive track of a ring-shaped current collector.

19. The device according to claim 18, wherein an opaque thin plate fixedly connected to the first support is positioned and oriented so as to interrupt a beam of light transmitted by an emitter of a fork sensor before said beam of light is received by a receiver of said fork sensor, when said first support is in a reference position corresponding to a specific azimuth angle of the incident light, and wherein said fork sensor emits a signal to the control unit when said beam of light is interrupted, the control unit controlling thereafter the second stepper motor in accordance with the difference between the predetermined azimuth angle of the incident light in a target position of the arc-shaped arm and said specific azimuth angle of the incident light so as to position said arc-shaped arm in said target position.

20. The device according to claim 19, wherein the fork sensor and the disc-shaped current collector are fixedly connected on a second support.

21. The device according to claim 20, wherein the first and second supports are each provided with a central aperture, said central apertures being aligned with the normal direction so as to permit the measurement by the measuring means of the light reflected by the subject in said normal direction.

22. The device according to claim 21, wherein the central apertures of the first and second supports are adapted to partially receive a lens of a camera.

* * * * *